United States Patent [19]

Kano et al.

[11] 3,933,828

[45] Jan. 20, 1976

[54] QUINONE DERIVATIVES AND COMPOSITIONS CONTAINING THE SAME

[75] Inventors: Hideo Kano, Ibaraki; Masaru Ogata, Kobe; Hisajiro Yukinaga, Kusatsu, all of Japan

[73] Assignee: Shionogi & Co., Ltd., Osaka, Japan

[22] Filed: Nov. 29, 1973

[21] Appl. No.: 419,970

Related U.S. Application Data

[62] Division of Ser. No. 220,708, Jan. 25, 1972, Pat. No. 3,855,168.

[30] Foreign Application Priority Data

Feb. 9, 1971 Japan................................. 46-5389
Feb. 9, 1971 Japan................................. 46-5390
Feb. 9, 1971 Japan................................. 46-5393
Mar. 31, 1971 Japan............................... 46-19410

[52] U.S. Cl.............. 260/288 R; 71/94; 260/288 D; 260/288 CF; 260/289 R; 260/289 D
[51] Int. Cl.$^2$....................................... C07D 215/20
[58] Field of Search................................. 260/288 R

[56] References Cited
UNITED STATES PATENTS 3,005,824 10/1961 Domazk et al................. 260/288 R

FOREIGN PATENTS OR APPLICATIONS 221,311 5/1962 Austria............................ 260/288 R

OTHER PUBLICATIONS

Joseph et al.; *Chem. Abstr.*, Vol. 62, Col. 5253a, 1965.

Morrocchi et al.; *Gazz. Chim. Ital.*, Vol. 98, pp. 891–906, 1968.

Morrocchi et al.; *Gazz. Chim. Ital.*, Vol. 99, pp. 565–581, 1969.

Taylor et al.; *Jour. Am. Chem. Soc.*, Vol. 94, pp. 2874–2875, 1972.

*Primary Examiner*—Donald G. Daus
*Assistant Examiner*—Mary C. Vaughn
*Attorney, Agent, or Firm*—Wenderoth, Lind & Ponack

[57] ABSTRACT

Novel quinone derivatives having plant-growth regulating activity and being prepared by light irradiation or catalylic reduction from isoxazole derivatives, and compositions containing the said quinone derivatives.

2 Claims, No Drawings

QUINONE DERIVATIVES AND COMPOSITIONS CONTAINING THE SAME

This is a division of application Ser. No. 220,708 filed Jan. 25, 1972, now U.S. Pat. No. 3,835,768.

The present invention relates to novel quinone derivatives and processes for their preparation. Further, it relates to compositions containing the quinone derivatives as active ingredients.

The said quinone derivatives may be represented by the following formula:

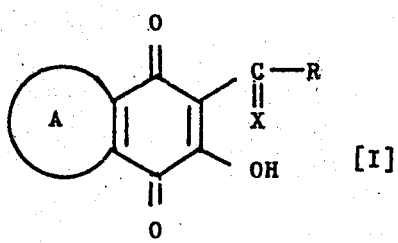

wherein R is a lower alkyl group (e.g. methyl, ethyl, propyl, isopyropyl, butyl, pentyl), a phenyl group or a pyridyl group; X is an amino group or a lower alkylimino group; A is a condensed benzene ring or a condensed pyridine ring; and where A and R may have one or more substituents selected from the group consisting of hydroxy group, lower alkyl groups (e.g. methyl, ethyl, propyl, isopropyl, butyl, pentyl), lower alkoxy groups (e.g. methoxy, ethoxy, propoxy, butoxy) and halogen atoms (e.g. chlorine, bromine, iodine).

The said quinone derivatives of the formula [I] are novel, and it has been discovered that they show plant-growth regulating activity.

Accordingly, a basic object of this invention is to provide novel quinone derivatives of the formula [I]. Another object of the invention is to provide quinone derivatives showing plant-growth regulating activity. A further object of the invention is to provide a process for preparing the novel quinone derivatives. A still further object is to provide plant-growth regulating compositions containing the quinone derivatives as active ingredients. These and other objects and the manner in which they are accomplished will become apparent to those conversant with the art from the following descriptions.

In one aspect of the invention, it relates to novel quinone derivatives which may be illustrated by the following formula:

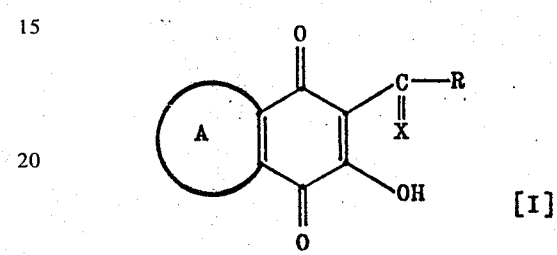

wherein R, X and A each has the same significance as designated above.

The preparation of the objective compounds [I] may be illustrated by the following scheme:

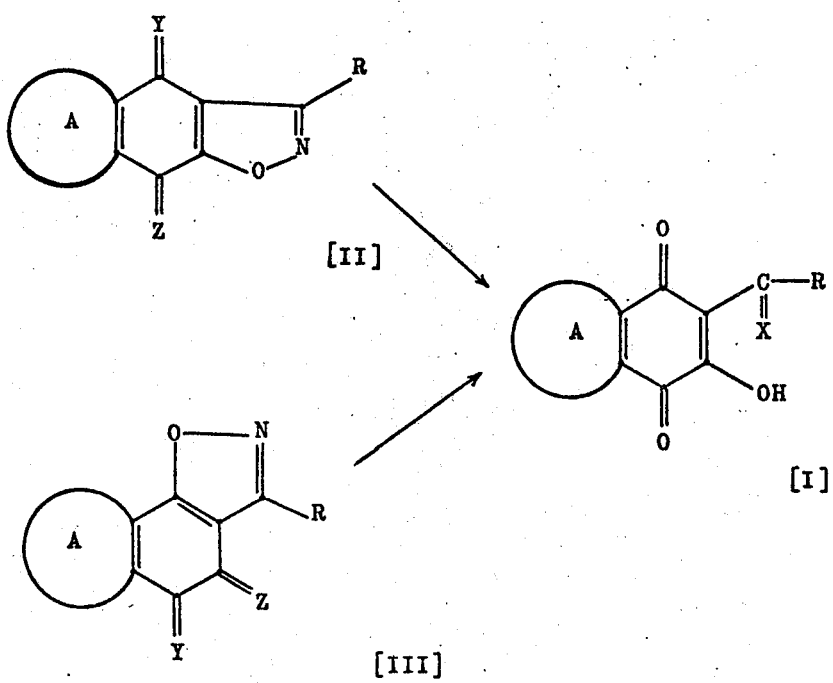

wherein Y and Z each is an oxygen atom or the group of

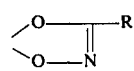

and R, X and A each has the same significance as designated above.

An illustrative of the objective compounds [I] are:
2-acetimidoyl-3-hydroxy-1,4-naphthoquinone, 2-acetimidoyl-3-hydroxy-6-methyl-1,4-naphthoquinone,
2-acetimidoyl-3-hydroxy-6,7-dimethoxy-1,4-naphthoquinone,
2-acetimidoyl-3-hydroxy-6-chloro-1,4-naphthoquinone,
2-acetimidoyl-3,7-dihydroxy-1,4-naphthoquinone,
2-propionimidoyl-3-hydroxy-1,4-naphthoquinone,
2-propionimidoyl-3-hydroxy-6-methoxy-1,4-naphthoquinone,
2-propionimidoyl-3-hydroxy-6,7-dichloro-1,4-naphthoquinone,
2-butyrimidoyl-3-hydroxy-1,4-naphthoquinone,
2-butyrimidoyl-3-hydroxy-6-methoxy-1,4-naphthoquinone,
2-butyrimidoyl-3-hydroxy-7-methyl-1,4-naphthoquinone,
2-benzimidoyl-3-hydroxy-1,4-naphthoquinone,
2-benzimidoyl-3-hydroxy-6,8-dichloro-1,4-naphthoquinone,
2-(3-methylbenzimidoyl)-3-hydroxy-1,4-naphthoquinone,
2-(4-methoxybenzimidoyl)-3-hydroxy-1,4-naphthoquinone,
2-(4-chlorobenzimidoyl)-3-hydroxy-6,7-dimethyl-1,4-naphthoquinone,
2-(3-methoxybenzimidoyl)-3-hydroxy-1,4-naphthoquinone,
2-benzimidoyl-3-hydroxy-7-methoxy-1,4-naphthoquinone,
2-(3,5-dibromobenzimidoyl)-3-hydroxy-1,4-naphthoquinone,
2-(3,5-dichlorobenzimidoyl)-6,7-dichloro-1,4-naphthoquinone,
2-(3-pyridylcarbimidoyl)-3-hydroxy-1,4-naphthoquinone,
2-(3-pyridylcarbimidoyl)-3-hydroxy-8-methoxy-1,4-naphthoquinone,
2-(N-methylbenzimidoyl)-3-hydroxy-1,4-naphthoquinone,
2-(N-methylbenzymidoyl)-3-hydroxy-6-chloro-1,4-naphthoquinone,
2-(N-methylbenzimidoyl)-3-hydroxy-6,7-dimethoxy-1,4-naphthoquinone,
2-(N-methyl-4-chlorobenzimidoyl)-3-hydroxy-8-propyl-1,4-naphthoquinone,
2-(N-methyl-3-pyridylcarbimidoyl)-3-hydroxy-1,4-naphthoquinone,
2-(N-ethylbenzimidoyl)-3-hydroxy-6-methyl-1,4-naphthoquinone,
2-(N-ethyl-3-chlorobenzimidoyl)-3-hydroxy-5-chloro-1,4-naphthoquinone,
2-(N-ethylbenzimidoyl)-3-hydroxy-7-methoxy-1,4-naphthoquinone,
2-(N-ethyl-3-pyridylcarbimidoyl)-3-hydroxy-1,4-naphthoquinone,
2-(N-propylbenzimidoyl)-3-hydroxy-1,4-naphthoquinone,
2-(N-propylbenzimidoyl)-3-hydroxy-6-methyl-1,4-naphthoquinone,
2-(N-propyl-3-pyridylcarbimidoyl)-3-hydroxy-1,4-naphthoquinone,
6-acetimidoyl-7-hydroxy-5,8-dihydroquinoline-5,8-dione,
6-benzimidoyl-7-hydroxy-5,8-dihydroquinoline-5,8-dione,
6-(3-pyridylcarbimidoyl)-7-hydroxy-5,8-dihydroquinoline-5,8-dione,
4-methoxy-6-benzimidoyl-7-hydroxy-5,8-dihydroquinoline-5,8-dione,
3-bromo-6-(3-bromobenzimidoyl)-7-hydroxy-5,8-dihydroquinoline-5,8-dione,
6-(N-methylbenzimidoyl)-7-hydroxy-5,8-dihydroquinoline-5,8-dione,
3-methyl-6-(N-ethylbenzimidoyl)-7-hydroxy-5,8-dihydroquinoline-5,8-dione,
6-(N-propyl-3-pyridylcarbimidoyl)-7-hydroxy-5,8-dihydroquinoline-5,8-dione,
6-hydroxy-7-acetimidoyl-5,8-dihydroquinoline-5,8-dione,
6-hydroxy-7-benzimidoyl-5,8-dihydroquinoline-5,8-dione,
3-chloro-6-hydroxy-7-(3-pyridylcarbimidoyl)-5,8-dihydroquinoline-5,8-dione.
6-hydroxy-7-(N-methylbenzimidoyl)-5,8-dihydroquinoline-5,8-dione,
4-methyl-6-hydroxy-7-(N-methyl-3-bromobenzimidoyl)-5,8-dihydroquinoline-5,8-dione,
6-hydroxy-7-(N-methyl-3-pyridylcarbimidoyl)-5,8-dihydroquinoline-5,8-dione,
6-butyrimidoyl-7-hydroxy-5,8-dihydroisoquinoline-5,8-dione,
6-(N-methylbenzimidoyl)-7-hydroxy-5,8-dihydroisoquinoline-5,8-dione,
6-hydroxy-7-benzimidoyl-5,8-dihydroisoquinoline-5,8-dione, and
6-hydroxy-7-propionimidoyl-5,8-dihydroisoquinoline-5,8-dione.

According to the present invention the objective quinone derivatives [I] can be prepared from corresponding isoxazole compounds of the formula [II] or [III] by two alternative methods except that the N-alkylated imidoyl compounds can be prepared only under specific conditions. One of these methods is light irradiation of the starting compounds in the presence of a hydrogen-donating agent, and the other is catalytic reduction of the starting compounds in the conventional manner. Details of these methods are explained below.

1. LIGHT IRRADIATION

The light irradiation of the starting compound [II] or [III] is carried out in the presence of a hydrogen-donating agent. For the purpose of preparation of N-unsubstituted imidoyl products, a hydrogen-donor such as water, an alcohol (e.g. methanol, ethanol, propanol, cyclohexanol) or the like is used. Many other substances (e.g. trialkyamines) may also be used for this purpose so long as they donate hydrogen atoms to effect the reductive cleavage of the isoxazole ring of the starting compound [II] or [III] under the light irradiation. If it is intended to produce N-alkylated imidoyl products, a primary or secondary alkylamine (e.g. methylamine, ethylamine, propylamine, dimethylamine, diethylamine, dipropylamine) should be used as the hydrogen-donating agent. In any case, the amount of the hydrogen donor to be used should be such as to provide sufficient hydrogen for the intended reductive cleavage, but an excess of the hyrogen-donor does not cause any unfavorable effect on the reaction.

Although the liquid hydrogen-donor, when used excessively, may also serve as the reaction solvent, there may be used, in addition to the hydrogen-donor, an inert solvent such as benzene, toluene, ether, tetrahydrofuran, dioxane, ethyl acetate or the like.

It may be noted that the reaction can be achieved in the vapor-phase by a conventional technique for vapor-phase reactions.

The light to be used is not limited to a specific range of wave lengths though the most effective range is from about 1800 A to about 4000 A. If desired, suitable filters may be used to cut off light of unfavorable wave lengths. As the light source there may be used, for example, a high-pressure mercury lamp, a low-pressure mercury lamp, a sterilization lamp (a kind of the low-pressure mercury lamps), a xenon arc lamp, or the like. Sunlight may also be available.

Control of the reaction temperature is not essential, but it is generally preferred to execute the reaction at a temperature ranging from about 0°C to about 80°C. In the reactions at a higher temperature, there is a tendency to an increase of unfavorable by-products. Since unfavorable side-reactions are also induced by oxygen, it is generally recommended to carry out the reaction in an inert atmosphere such as nitrogen, argon or the like. Usually, the reaction may be completed within a period of 1 to 20 hours, but this depends on the reaction temperature, the light source and other conditions.

2. CATALYTIC REDUCTION

By the catalytic reduction method, only the N-unsubstituted imidoyl compounds can be produced. The catalytic reduction may be carried out in a conventional manner. Generally, it is executed at a temperature ranging from about 0°C to about 100°C under ordinary (atmospheric) pressure, until an approximately theoretical amount of hydrogen is taken up. For this reduction, there can be employed any of the conventional catalysts for catalytic reduction. They include, for example, palladium, platinum, nickel, cobalt, iron, and copper catalysts, which may be used in the form of colloids, oxides, Raney catalysts, and the like with or without a carrier. The reaction solvent may be selected from, for example, water, methanol, ethanol, ethylene glycol, acetic acid, ethyl acetate, ether, tetrahydrofuran, dioxane, benzene, cyclohexane and the like in consideration of the solubility of the starting compound as well as the properties of the catalyst employed.

The starting compounds [II] or [III] can be prepared, for instance, by condensing quinone derivatives with nitrile oxide according to the methods described in *Gazz Chim. Ital.*, 80, 140 (1950), *Gazz. Chim. Ital.* 98, 891 (1968) and *Gazz. Chim. Ital.* 99, 565 (1969), as illustrated below.

A. Preparation of 1,4-quinone type compounds:

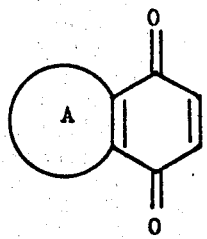  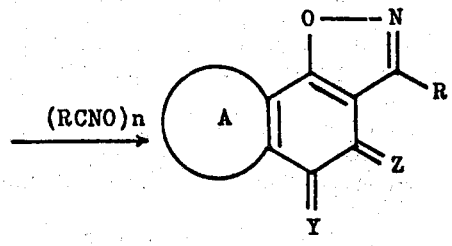

B. Preparation of 1,2-quinone type compounds:

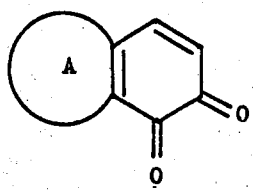

wherein R, A, Y and Z each has the same significance as designated above and n is an integer from 1 to 3.

Examples of the starting compounds are:

3-methyl-4,9-dihydronaphtho[2,3-d]isoxazole-4,9-dione,
3,7-dimethyl-4,9-dihydronaphtho[2,3-d]isoxazole-4,9-dione,
3-methyl-7,8-dimethoxy-4,5-dihydronaphtho[2,1-d]isoxazole-4,5-dione,
3,5'-dimethyl-7-chloro-4,9-dihydronaphtho[2,3-d]isoxazole-9-spiro-2'-1'3',4'-dioxazol-4-one,
3,5'-dimethyl-8-hydroxy-4,5-dihydronaphtho[2,1-d]isoxazole-5-spiro-2'-1',3'-4'-dioxazol-4-one,
3-ethyl-4,9-dihydronaphtho[2,3-d]isoxazole-4,9-dione,
3-ethyl-7-methoxy-4,9-dihydronaphtho[2,3-d]isoxazole-4,9-dione,
3-ethyl-7,8-dichloro-4,5-dihydronaphtho[2,1-d]isoxazole-4,5-dione,
3,5'-dipropyl-4,9-dihydronaphtho[2,3-d]isoxazole-9-spiro-2'-1',3',4'-dioxazol-4-one,
3,5'-dipropyl-7-methoxy-4,5-dihydronaphtho[2,1-d]isoxazole-5-spiro-2'-1',3',4'-dioxazol-4-one,
3,5',5''-tripropyl-6-methyl-4,9-dihydro-1'',3'',4''-dioxazole-2''-spiro-4-naphtho[2,3-d]isoxazole-9-spiro-2'-1',3',4'-dioxazole,
3-phenyl-4,9-dihydronaphtho[2,3-d]isoxazole-4,9-dione,
3-phenyl-7,9-dichloro-4,5-dihydronaphtho[2,1-d]isoxazole-4,5-dione,
3,5'-di-(3-methylphenyl)-4,9-dihydronaphtho[2,3-d]isoxazole-9-spiro-2'-1',3',4'-dioxazol-4-one,
3,5'-di-(4-methoxyphenyl)-4,5-dihydronaphtho[2,1-d]isoxazole-5-sprio-2'-1',3',4'-dioxazol-4-one,
3,5',5''-tri-(4-chlorophenyl)-6,7-dimethyl-4,9-dihydro-1'',3'',4''-dioxazole-2''-spiro-4-naphtho[2,3-d]isoxazole-9-spiro-2'-1',3',4'-dioxazole,
3-(3-methoxyphenyl)-4,9-dihydronaphto[2,3-d]isoxazole-4,9-dione, 3-phenyl-6-methoxy-4,9-dihydronaphtho[2,3-d]isoxazole-4,9-dione,
3-(3,5-dibromophenyl)-4,5-dihydronaphtho[2,1-d]isoxazole-4,5-dione,
3,5'-di-(3,5-dichlorophenyl)-6,7-dichloro-4,9-dihydronaphtho-[2,3-d]isoxazole-9-spiro-2'-1',3',4'-dioxazol-4-one,
3,5'--di(3-pyridyl)-4,5-dihydronaphtho[2,1-d]isoxazole-5-spiro-2'-1',3',4'-dioxazol-4-one,
3-(3-pyridyl)-5-methoxy-4,9-dihydronaphtho[2,3-d]isoxazole-4,9-dione,
3-phenyl-6,7-dimethoxy-4,9-dihydronaphtho[2,3-d]isoxazole-4,9-dione,
3,5'-di-(4-chlorophenyl)-5-propyl-4,9-dihydronaphtho[2,3-d]-isoxazole-9-spiro-2'-1', 3',4'-dioxazol-4-one,
3,5'-diphenyl-7-methyl-4,5-dihydronaphtho[2,1-d]isoxazole-5-spiro-2'-1',4'-dioxazol-4-one,
3,5'-di-(3-chlorophenyl)-6-chloro-4,5-dihydronaphtho[2,1-d]-isoxazole-5-spiro-2'-1',3',4'-dioxazol-4-one,
3-methyl-4,9-dihydroisoxazolo[4,5-g]quinoline-4,9-dione,
3-phenyl-4,9-dihydroisoxazolo[4,5-g]quinoline-4,9-dione,
3-(3-pyridyl)-4,5-dihydroisoxazolo[5,4-f]quinoline-4,5-dione,
3-phenyl-9-methoxy-4,5-dihydroisoxazolo[5,4-f]quinoline-4,5-dione,
3,5'-di-(3-bromophenyl)-6-bromo-4,9-dihydroisoxazolo[4,5-g]-quinoline-9-spiro-2'-1',3',4'-dioxazol-4-one,
3,5',5''-triphenyl-4,9-dihydro-1'',3'',4''-dioxazole-2''-spiro-4-isoxazolo[4,5-g]quinoline-9-spiro-2'-1',3',4'-dioxazole,
3,5'-diphenyl-8-methyl-4,5-dihydrosoxazolo[5,4-f]quinoline-5-spiro-2'-1',3',4'-dioxazol-4-one,
3,5'-di-(3-pyridyl)-4,5-dihydroisoxazolo[5,4-f]quinoline-5-spiro-2'-1',3',4'-dioxazol-4-one,
3-methyl-4,9-dihydroisoxazole[5,4-g]quinoline-4,9-dione,
3-phenyl-4,9-dihydroisoxazolo[5,4-g]quinoline-4,9-dione,
3-(3-pyridyl)-7-chloro-4,5-dihydroisoxazolo[4,5-h]quinoline 4,5-dione,
3-phenyl-4,5-dihydroisoxazolo[4,5-h]quinoline-4,5-dione,
3,5'-di-(3-bromophenyl)-8-methyl-4,9-dihydroisoxazolo[5,4-g]-quinoline-9-spiro-2'-1',3',4'-dioxazolo-4-one,
3-(3-pyridyl)-4,9-dihydroisoxazolo[5,4-g]quinoline-9-spiro2'-1', 3',4'-dioxazol-4-one,
3-propyl-4,9-dihydroisoxazolo[4,5-g]isoquinoline-4,9-dione,
3-phenyl-4,5-dihydroisoxazolo[5,4-f]isoquinoline-4,5-dione,
3-phenyl-4,9-dihydroisoxazolo[5,4-g]isoquinoline-4,9-dione, and 3-ethyl-4,5-dihydroisoxazolo[4,5-h]isoquinoline-4,5-dione.

In another aspect of the invention, it relates to plant-growth regulant compositions containing an effective amount of the novel quinone derivative [I] in combination with suitable agricultural carriers and other ingredients, the composition being suited to application in a variety of forms for modification or regulation of plant-growth patterns.

It has been confirmed that the quinone derivatives have plant-growth stimulating effect by the straight growth tests on *Avena coleoptiles* in which they showed an apparent growth stimulation at concentrations from about 0.1 μg/ml to about 10 82 /ml. Thus, they show auxin activity at concentrations of this range. On the other hand, the quinone derivatives [I] show herbicidal or algicidal activity against various weeds and algae including, for example, *Monochoria vaginalis, Rotala indica, Vandellia angustifolia, Cyperus difformis, Spirogyra arcla* and *Oedogonium sp.*, when applied at a level of about 10 grams per are to about 80 grams per are, but are inactive to gramineous plants even at the same or slightly higher level. Thereofre, they can be used at this level as a selective herbicide or algicide. Although the quinone derivatives [I] have these and other growth-regulating activities as a plant hormone, the most important and characteristic feature they show is parthenocarpy-stimulating activity.

As is well known, parthenocarpy-stimulating agents are important in cultivation of fruit in the green house. It has been discovered that the quinone derivatives [I] show excellent parthenocarpy-stimulating activity against various fruits such as tomato, eggplant, cucumber, melon, water melon and the like. To illustrate the parthenocarpy-stimulating effect, the test results with tomato are shown in the following table.

Parthenocarpy-stimulating Effects of Some Typical Quinone Derivatives [I]

| Test Compound | Test Variety of Tomato | Concentration (μg/ml) | Number of Flower Treated | Number of Fruit Developed | Percentage of Parthenocarpy |
|---|---|---|---|---|---|
| 2-Benzimidoyl-3-hydroxy-1,4-naphthoquinone | "Miniature" | 50 | 43 | 10 | 23.3 |
| " | " | 100 | 44 | 20 | 45.5 |
| " | " | 250 | 32 | 24 | 75.0 |
| " | "Fukuju No. 2" | 50 | 20 | 8 | 40.0 |
| " | " | 100 | 24 | 23 | 95.8 |
| " | " | 250 | 25 | 24 | 96.0 |
| 2-(N-methylbenzimidoyl)-3-hydroxy-1,4-naphthoquinone | "Miniature" | 100 | 49 | 26 | 53.1 |
| 2-(4-Methoxybenzimidoyl)-3-hydroxy-1,4-naphthoquinone | "Fukuju No.2" | 50 | 18 | 17 | 94.4 |
| 6-Hydroxy-7-benzimidoyl-5,8-dihydroquinoline-5,8-dione* | " | 50 | 12 | 7 | 58.3 |
| 2-(3-Pyridylcarbimidoyl)-3-hydroxy-1,4-naphthoquinone | " | 50 | 10 | 7 | 70.0 |

*Or 6-benzimidoyl-7-hydroxy-5,8-dihydroquinoline-5,8-dione

TEST METHODS

1. With "Miniature" tomato: When two or three of the first flower clusters began to flower, their stamens were removed, and the clusters were covered by paper bags to prevent pollination from non-emasculated flowers. The test solution was prepared by dissolving the test compound at a predetermined concentration in water together with 100 μ/ml of Tween 20. On the day after the removal of stamens, the test solution was sprayed onto the flower clusters. The number of developed fruit was counted after the fruit had colored, and parthenocarpy was confirmed by the fact that the fruit had no seeds.

2. With "Fukuju No. 2" tomato: When two or three of the first flower clusters began to flower, their stamens and stigmas were removed. Then, the flowers were soaked in test solution prepared in the same manner as described above. The number of developed fruit was counted after the fruit had colored, and parthenocarpy was confirmed by the fact that the fruit had no seeds.

It is apparent from the table that the test compounds have marked parthenocarpy-stimulating activity. In addition, it has been confirmed that they show no phyto-toxicity against the test plant and that the fruit harvested is not inferior to those obtained by natural pollination either in size or in weight.

Since the other quinone derivatives of the present invention not listed in the table also show similar biological activity, all the quinone derivatives [I] are extremely useful as parthenocarpy-stimulating agents.

The plant-growth regulating compositions of the present invention may be prepared in various conventional forms such as aerosols, solutions, emulsions, emulsifiable concentrates, wettable powders, pastes, dusts, granules, pellets, tablets or the like according to the use intended. The composition may normally contain from about 0.00001 percent by weight to about 90 percent by weight of the quinone derivative [I] as an active ingredient, the amount contained depending on the form of composition as well as the use intended. To formulate the composition, suitable gaseous, liquid, or solid carriers and other ingredients including surface active agents are used in addition to one or more compounds of the quinone derivatives [I], and conventional techniques for mixing, blending, crushing, granulating, or tabletting may optionally be adopted.

The surface active agents used in preparing the compositions of the present invention can be wetting, dispersing, or emulsifying agents. They may act, for example, as wetting, agents for wettable powders and dusts, as despersing agents for wettable powders and suspensions, and as emulsifying agents for emulsions and emulsifiable concentrates. Surfactants may also enhance the biological activity of the activity ingredients.

Suitable surface active agents for use in the compositions include polyethylene glycol esters with fatty acids; polyethylene glycol ethers with alkylphenols or with long-chain aliphatic alcohols; polyethylene glycol ethers with sorbitan fatty acid esters; and polyoxyethylenethio ethers. Other suitable surfactants include ammonium, alkali, or alkaline earth salts of alkylaryl sulfonic acids; ammonium, alkali, or alkaline earth fatty alcohol sulfates; fatty acid esters of ammonium, alkali, or alkaline earth isothionates or taurates; ammonium, alkali, or alkaline earth salts of lignin sulfonic acids; methylated or hydroxyethylated cellulose; polyvinyl alcohols; alkyl-substituted polyvinyl pyrrolidones; ammonium, alkali, or alkaline earth salts of polymerized alkylnaphthalene sulfonic acids; and long-chain quaternary ammonium compounds.

Examples of gaseous carriers include butane, nitrogen, carbon dioxide, freon, and other inert gases. Liquid carriers for the present composition may be water, or suitable inert organic solvent such as aliphatic hydrocarbons (e.g. pentane, hexane, cyclohexane, petroleum ether, gasoline, kerosene), aromatic hydrocarbons (e.g. benzene, toluene, xylene), halogenated hydrocarbons (e.g. methylene chloride, chloroform, carbon tetrachloroide trichloroethane), ketones (e.g. acetone, methyl ethyl ketone), ethers (e.g. ether, isopropyl ether, tetrahydrofuran, dioxane), esters (e.g. ethyl acetate, amyl acetate) or alcohols (e.g. methanol, ethanol, butanol). Solid carriers may be, for example, mineral powders (e.g. clay, talc, kaoline, bentonite, diatomaceous earth, silica gel), vegetable powders (e.g. soybean powder, wheat powder), or other powders conventionally used as agricultural solid carriers or diluents.

More particularly, preferred forms of the composition of the present invention for use as a parthenocarpy-stimulating agent may be solutions, emulsions, emulsifiable concentrates or wettable powders. They may be diluted before application to a concentration of from about 1 μg/ml to about 1,000 μg/ml and sprayed on the objective plants at a stage of flowering. To ensure such effect, it may be recommended to repeat the treatment two or three times in the same day or over two or three days, though the full effect can usually be obtained by a single treatment.

If desired, the compositions of the present invention may contain, in addition to one or more of the quinone derivatives [I], other plant-regulants, plant hormones, germicides, pesticides, insecticides, acaricides, nematocides, fertilizers or the like.

The following examples are given solely for the purpose of illustration and not to be construed as limitation of this invention, many variations of which are possible.

EXAMPLE 1

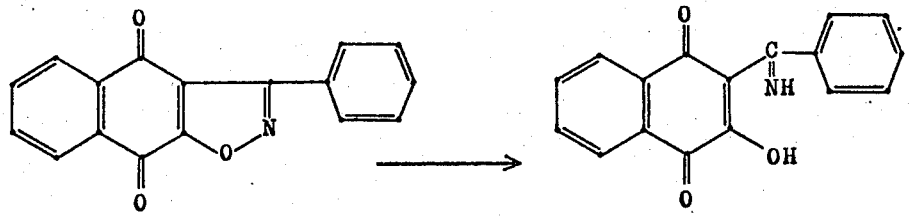

A. A solution of 3-phenyl-4,9-dihydronaphtho-[2,3-d]isoxazole-4,9-dione (m.p. 133°–135°C, 500 mg) in methanol (400 ml) is irradiated by light of a low-pressure mercury lamp (35 W) at room temperature (20°–30°C) for 3 hours in argon atmosphere. After removal of methanol, the residue is extracted with chloroform. The extract is chromatographed on alumina. The chloroform insoluble residue is dissolved in a mixture of chloroform and methanol, and this solution is also chromatograped on alumina. The fractions containing the objective compound are combined, evaporated, and the residue is recrystallized from 70 % acetic acid to give 2-benzimidoyl-3-hydroxy-1,4-naphthoquinone (315 mg) as pale yellow scales, m.p. 258°14 259°C.

Anal. Calcd. for $C_{17}H_{11}O_3$ N: C, 73.64; H, 4.00; N, 5.05.

Found: C, 73.83; H, 3.73; N, 4.89.

B. To a solution of 3-phenyl-4,9-dihydronaphtho-[2,1-d]isoxazole-4,5-dione (100 mg) in ethyl acetate (20 ml) is added platinum oxide (50 mg), and the mixture is subjected to catalytic reduction procedure at room temperature (20°–30°C) under atmospheric pressure for 2 hours. After removal of the catalyst, the ethyl acetate is evaporated. The residue is chromatographed on alumina. Elution with methylene chloride gives the starting material (25 mg). Subsequent elution with methylene chloride-methanol (20:1) followed by treatment with isopropyl ether gives 2-benzimidoyl-3-hydroxy-1,4-naphthoquinone (8 mg). Recrystallization from 80% acetic acid gives pale yellow scales, m.p. 258°–259°C, identical with the product of Example 1.

EXAMPLE 3

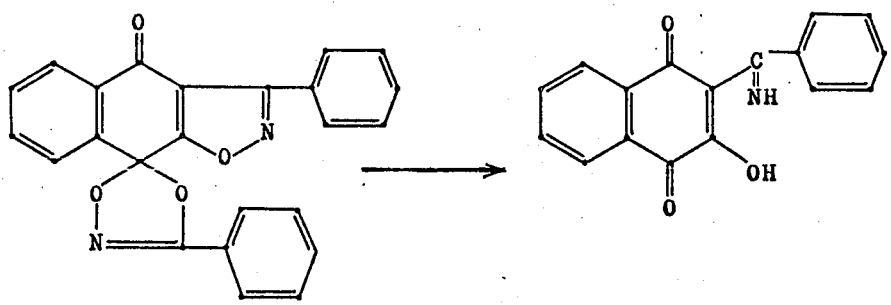

[2,3-d]isoxazole-4,9-dione (m.p. 133°–135°C, 2.0 g) in ethanol (200 ml) is added Raney nickel prepared from 50 % Raney-Nickel alloy (3 g). The mixture is subjected to catalytic reduction procedure at room temperature (20°–30°C) under atmospheric pressure. After completion of hydrogen absorption, the catalyst is removed by filtration and the ethanol is evaporated. The residue is chromatographed on alumina and eluted with methylenechloride-methanol (95:5). The yellowish crystals obtained are washed with ether-ethyl acetate and recrystallized from 80 % acetic acid to give 2-benzimidoyl-3-hydroxy-1,4-naphthoquinone (1.01 g) as pale yellow scales, m.p. 258°–259°C, which is identical with the product of the part [A] above.

EXAMPLE 2

A. A solution of 3,5'-diphenyl-4,9-dihydronaphtho-[2,3-d]isoxazole-9-spiro-2'-1',3',4'-dioxazol-4-one (200 mg) in methanol (400 ml) is irradiated by light of a high-pressure mercury lamp(450 W) through a pyrex filter at room temperature (20°–30°C) for 1 hour in argon atmosphere. After removal of the methanol, the residue is chromatographed on alumina and eluted with benzene and benzene-methylene chloride (1:1) to give an intermediary product, 3-phenyl-4,9-dihydronaphtho[2,3-d]isoxazole-4,9-dione (2 mg). Subsequent elution with methylene chloride-methanol (20:1) gives 2-benzimidoyl-3-hydroxy-1,4-naphthoquinone (20 mg), identical with the product of Example 1.

B. To a solution of 3,5'-diphenyl-4,9-dihydronaphtho[2,3,-d]isoxazole-9-spiro-2'-1',3',4'-dioxazol-4-one

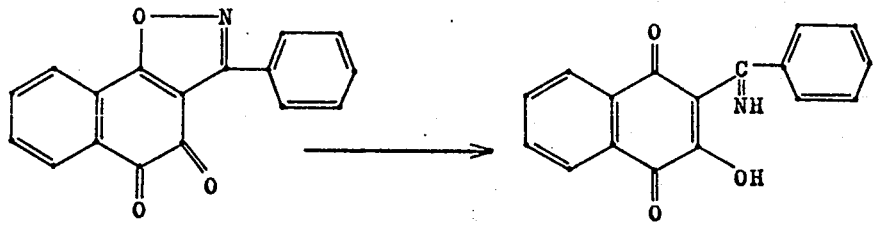

A. A solution of 3-phenyl-4,5-dihydronaphtho-[2,1-d]isoxazole-4,5-dione (40 mg) in methanol (40 ml) is irradiated by light of a high-pressure mercury lamp (1 KW) at room temperature (20°–30°C) for about 1 hour. After removal of the solvent, the residue is chromatographed on alumina and eluted with methylene chloride-methanol (20:1). The eluate is evaporated and the residue is washed with isopropyl ether-ether to give 2-benzimidoyl-3-hydroxy-1,4-naphthoquinone (23 mg). Recrystallization from acetic acid gives pale yellow scales, m.p. 258°–259°C, identical with the product of Example 1.

B. To a suspension of 3-phenyl-4,5-dihydronaphtho- (500 mg) in ethyl acetate (84 ml) is added platinum oxide (100 mg), and the mixture is subjected to catalytic reduction procedure at room temperature (20°14 30°C) under atmospheric pressure. After completion of hydrogen absorption, the catalyst is removed by filtration, and the ethyl acetate is evaporated. The residue is chromatographed on alumina and eluted with methylene chloride-methanol (20:1). The eluate is evaporated, the residue is washed with ethyl acetate, and the precipitate is collected by filtration. Recrystallization from methanol gives 2-benzimidoyl-3-hydroxy-1,4-naphthoquinone (38 mg), which is identical with the product of Example 1.

EXAMPLE 4

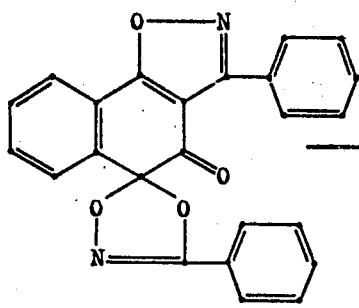 → 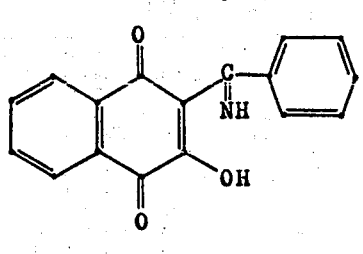

A. A solution of 3,5'-diphenyl-4,5-dihydronaphtho[2,1-d]isoxazole-5-spiro-2'-1',3',4'-dioxazol-4-one (500 mg) in methanol (150 ml) is irradiated by light of a high-pressure mercury lamp through a pyrex filter at room temperature (20°–30°C) for 7 hours in argon atmosphere. Work-up in a similar manner to that described in Example 1 [A] gives 2-benzimidoyl-3-hydroxy-1,4-naphthoquinone (25 mg), identical with the product of Example 1.

B. To a solution of 3,5'-diphenyl-4,5-dihydronaphtho[2,1-d]isoxazole-5-spiro-2'-1',3',4'-dioxazol-4-one (124 mg) in ethyl acetate (25 ml) is added platinum oxide (40 mg), and the mixture is subjected to catalytic reduction procedure at room temperature (20°–30°C) under atmospheric pressure. After completion of hydrogen absorption, the catalyst is removed by filtration, the ethyl acetate is evaporated, and the residue is chromatographed on alumina. Work-up in a similar manner to that described in Example 1 [B] gives 2-benzimidoyl-3-hydroxy-1,4-naphthoquinone (20 mg), identical with the product of Example 1.

EXAMPLES 5 – 9

The products listed below can be prepared by substantially the same procedure as Example 1 [A] from the corresponding starting compounds.

| Ex. No. | Starting compound | Light source (Solvent) | Product M.P. |
|---|---|---|---|
| 5 | 3-Phenyl-4,9-dihydronaphtho[2,3-d]isoxazole-4,9-dione | High-pressure mercury lamp (1 KW) through a pyrex filter (Trimethylamine-Dioxane) | 2-Benzimidoyl-3-hydroxy-1,4-naphthoquinone 258–259°C |
| 6 | 3-(4-Methylphenyl)-4,9-dihydronaphtho[2,3-d]isoxazole-4,9-dione | Low-pressure mercury lamp (35 W) (Methanol) | 2-(4-Methylbenzimidoyl)-3-hydroxy-1,4-naphthoquinone 250–254°C |
| 7 | 3-Methyl-4,9-dihydronaphtho[2,3-d]isoxazole-4,9-dione | High-pressure mercury lamp (1 KW) through a pyrex filter (Methanol) | 2-Acetimodyl-3-hydroxy-1,4-naphthoquinone 284°C(decomp.) |
| 8 | 3-(Pyridyl)-4,9-dihydronaphtho[2,3-d]-isoxazole-4,9-dione | High-Pressure mercury lamp (450 W)through a pyrex filter (Methanol) | 2-(3-Pyridylcarbimidoyl)-3-hydroxy-1,4-naphthoquinone 280–287°C |
| 9 | 3-Phenyl-4,9-dihydroisoxazole[4,5 or 5,4-g]-quinoline-4,9-dione | High pressure mercury lamp (450 W) through a pyrex filter (Methanol) | 6- (or 7-)Benzimidoyl-7- (or 6-)-hydroxy-5,8-dihydroquinoline-5,8-dione* 291–295°C |

*It has not been determined which of the two structural isomers the product is.

EXAMPLES 10 – 15

The products listed below can be prepared by substantially the same procedure as Example 1 [B] from the corresponding starting compounds.

| Ex. No. | Starting compound | Solvent and Catalyst | Product M.P. |
|---|---|---|---|
| 10 | 3-(4-Methylphenyl)-4,9-dihydronaphtho[2,3-d]-isoxazole-4,9-dione | Ethyl acetate Platinum oxide | 2-(4-Methylbenzimidoyl)-3-hydroxy-1,4-naphthoquinone 262°C |
| 11 | 3-(4-Methoxyphenyl)-4,9-dihydronaphtho-[2,3-d]isoxazole-4,9-dione | Ethyl acetate Platinum oxide | 2-(4-Methoxybenzimidoyl)-3-hydroxy-1,4-naphthoquinone 223–224.5°C |
| 12 | 3-(4-Chlorophenyl)-4,9-dihydronaphtho[2,3-d]-isoxazole-4,9-dione | Ethyl acetate Platinum oxide | 2-(4-Chlorobenzimidoyl)-3-hydroxy-1,4-naphthoquinone 276–277°C |
| 13 | 3-(4-Chlorophenyl)-6,7-dimethyl-4,9-dihydro- | Ethyl acetate Platinum oxide | 2-(4-Chlorobenzimidoyl)-3-hydroxy- |

| Ex. No. | Starting compound | Solvent and Catalyst | Product M.P. |
|---|---|---|---|
| | naphtho[2,3-d]isoxazole-4,9-dione | | 6,7-dimethyl-1,4-naphthoquinone 298–300°C |
| 14 | 3-(2,4-Dichlorophenyl)-6,7-dimethyl-4,9-dihydronaphtho[2,3-d]-isoxazole-4,9-dione | Ethyl acetate Platinum oxide | 2-(2,4-Dichlorobenz-imidoyl)-3-hydroxy-6,7-dimethyl-1,4-naphthoquinone 214–219°C |
| 15 | 3-Phenyl-6,7-dimethoxy-4,9-dihydronaphtho-[2,3-d]isoxazole-4,9-dione | Ethyl acetate Platinum oxide | 2-Benzimidoyl-3-hydroxy-6,7-dimethoxy-1,4-naphthoquinone 281–282°C(decomp.) |

EXAMPLE 16

A solution of 3-phenyl-4,9-dihydronaphtho[2,3-d]-isoxazole-4,9-dione (1.0 g) in 6.6 % dimethylamine-

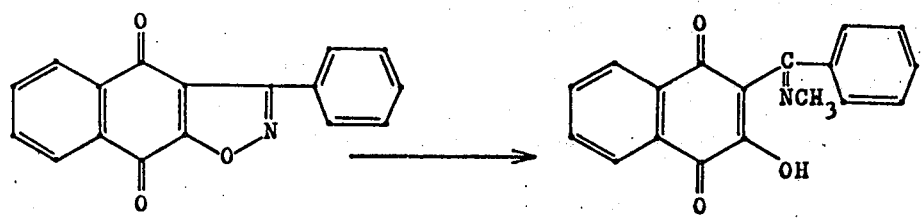

dioxane solution (100 ml) is irradiated by light of a high-pressure mercury lamp (1 KW) through a pyrex filter at room temperature (20°–30°C) in argon atmosphere for 3.3 hours. After removal of the solvent, the residue is dissolved in methylene chloride. The solution is washed with water, dried with anhydrous sodium sulfate, and evaporated. The residue is washed with benzene to give 2-(N-methylbenzimidoyl)-3-hydroxy-1,4-naphthoquinone (252 mg). Recrystallization from methanol gives yellow prisms, m.p. 235°–237°C.

Anal. Calcd. for $C_{18}H_{13}O_3N$: C, 74.21; H, 4.50; N, 4.81; Found: C, 74.49; H, 4.57; N, 4.65.

EXAMPLE 17

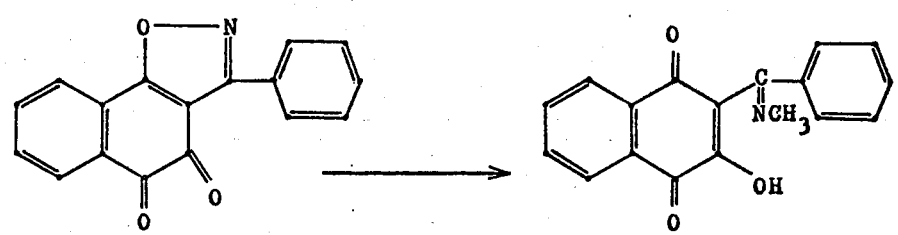

A solution of 3-phenyl-4,5-dihydronaphtho[2,1-d]-isoxazole-4,5-dione (500 mg) in 8 % dimethylamine-dioxane solution (100 ml) is irradiated by light of a high-pressure mercury lamp (1 KW) through a pyrex filter at room temperature (20–30°C) in argon atmosphere for about 1.5 hours. After removal of the solvent, the residue is dissolved in methylene chloride, washed with water, dried with anhydrous sodium sulfate, and evaporated. The residue is washed with benzene to give 2-(N-methylbenzimidoyl)-3-hydroxy-1,4-naphthoquinone (158 mg), which is identical with the product of Example 16.

EXAMPLE 18

An emusifiable concentrate of the following composition is prepared:

| | |
|---|---|
| 2-Benzimidoyl-3-hydroxy-1,4-naphthoquinone | 10 % by weight |
| Polyoxyethylene alkylaryl ether | 10 % by weight |
| Acetone | 80 % by weight |

The emulsifiable concentrate is diluted 200- to 1,000-fold with water before application for parthenocarpy stimulation.

EXAMPLE 19

An emulsifiable concentrate of the following composition is prepared:

| | |
|---|---|
| 2-(4-Methoxybenzimidoyl)-3-hydroxy-1,4-naphthoquinone | 10 % by weight |
| Polyoxyethylene alkylaryl ether | 10 % by weight |
| Methylnaphthalene | 80 % by weight |

The emulsifiable concentrate is diluted 200- to 10,000-fold with water before application for parthenocarpy stimulation.

EXAMPLE 20

An emulsifiable concentrate of the following composition is prepared:

| | |
|---|---|
| 2-(4-Methylbenzimidoyl)-3-hydroxy-1,4-naphthoquinone | 10 % by weight |
| Alkylphenyl ethyleneoxide | 5 % by weight |
| Acetone | 50 % by weight |
| Benzene | 35 % by weight |

The emulsifiable concentrate is diluted 200- to 10,000-fold with water before application for parthenocarpy stimulation.

EXAMPLE 21

A dust of the folllowing composition is prepared:

| | |
|---|---|
| 2-(3-Pyridylcarbimidoyl)-3-hydroxy-1,4-naphthoquinone | 1 part by weight |
| A mixture of talc and kaoline | 99 parts by weight |

The mixture is blended and ground to obtain a dust.

EXAMPLE 22

A mixture of the following composition is prepared:

| | |
|---|---|
| 6-Hydroxy-7-benzimidoyl-5,8-dihydroquinoline-5,8-dione | 20 % by weight |
| Bentonite powder | 80 % by weight |

After blending, the mixture is kneaded with water, granulated, and dried to obtain granules.

What is claimed is:
1. The compound 6-hydroxy-7-benzimidoyl-5,8-dihydroquinoline-5,8-dione.
2. The compound 6-benzimidoyl-7-hydroxy-5,8-dihydroquinoline-5,8-dione.

* * * * *